US008452609B2

(12) United States Patent  
Berg

(10) Patent No.: US 8,452,609 B2  
(45) Date of Patent: May 28, 2013

(54) COMPUTER SYSTEM FOR RULE-DRIVEN EMERGENCY DEPARTMENT CODING

(76) Inventor: Elijah Berg, Newton, MA (US)

(*) Notice: Subject to any disclaimer, the term of this patent is extended or adjusted under 35 U.S.C. 154(b) by 311 days.

(21) Appl. No.: 12/566,158

(22) Filed: Sep. 24, 2009

(65) Prior Publication Data

US 2010/0083175 A1    Apr. 1, 2010

Related U.S. Application Data

(60) Provisional application No. 61/099,630, filed on Sep. 24, 2008.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | | |
|---|---|---|---|
| 7,500,178 B1* | 3/2009 | O'Donnell | 715/221 |
| 2003/0212576 A1* | 11/2003 | Kim | 705/2 |
| 2004/0039757 A1* | 2/2004 | McClure | 707/201 |
| 2004/0254816 A1* | 12/2004 | Myers | 705/2 |
| 2005/0251422 A1* | 11/2005 | Wolfman et al. | 705/2 |
| 2006/0061806 A1* | 3/2006 | King et al. | 358/1.15 |
| 2006/0074719 A1* | 4/2006 | Horner | 705/3 |
| 2006/0268352 A1* | 11/2006 | Tanigawa et al. | 358/403 |
| 2008/0205742 A1* | 8/2008 | Lund | 382/141 |

* cited by examiner

*Primary Examiner* — Joseph Burgess
(74) *Attorney, Agent, or Firm* — Westerman, Hattori, Daniels & Adrian, LLP

(57) ABSTRACT

Among other things, the preferred embodiments provide a computer system whereby Coders can quickly and efficiently review, manage and modify patient record documentation electronically via a graphical user interface (GUI) provided on a computer display or monitor. In this manner, the Coder(s) can create electronic data files and Charge Reports that are used, e.g., by facilities to effect billing to patients and to prepare documentation to seek reimbursement from medical facilities.

25 Claims, 16 Drawing Sheets

FIG. 2

| LFName | NewCoder | Management | Mentor | Location | Expr1 |
|---|---|---|---|---|---|
| SDULAY | N | Y | Y | R | SDulay |
| JLESLEY | N | N | N | R | JLesley |
| KCREANE | N | N | N | I | KCreane |
| STOPALOVIC | N | N | N | R | STopalovic |
| LHENNIGER | N | Y | N | R | LHenniger |
| JHEBERT | Y | Y | N | I | JHebert |
| AHOGAN | N | N | N | R | AHogan |
| LMCDOWELL | N | N | N | R | LMcDowell |
| AJUERS | N | Y | N | R | AJuers |
| VKEEBLER | Y | N | N | R | VKeebler |
| JENH | N | Y | Y | I | JHebert |
| WFEASTER | Y | N | N | R | WFeaster |
| TTATE | Y | N | N | R | TTate |
| BLEBLANC | N | N | Y | I | BLeBlanc |
| KLEBLANC | N | Y | N | I | KLeBlanc |
| JNOTHSTINE | Y | N | N | R | JNothstine |
| KKAEHR | N | N | Y | R | KKaehr |
| MMORRIS | N | N | N | R | MMorris |
| LNICHOLS | N | N | N | R | LNichols |
| PTRUSKY | N | N | Y | R | PTrusky |
| DSTRIFE | N | N | N | R | DStrife |
| STODT | N | Y | N | R | STodt |
| BVIGIL | N | N | N | R | BVigil |
| DWILSON | N | Y | N | R | DWilson |
| PWICKLIFFE | N | N | Y | R | PWickliffe |
| RSTILLWELL | N | Y | N | I | RStillwell |
| ABAUGUS | N | N | N | R | ABaugus |
| PMCCAIN | N | N | N | R | PMcCain |
| KROHNER | N | N | N | R | KRohner |
| DREED | N | N | N | R | DReed |
| DSANDERS | Y | N | N | R | DSanders |
| EDUNAWAY | N | N | N | R | EDunaway |
| SBOTKIN | N | N | Y | R | SBotkin |
| TMACHADO | N | Y | N | I | TMachado |
| LGOOLSBY | Y | N | N | R | LGoolsby |

Unable to Code Reason

When choosing Unable to Code, please fill out as much of the coding template as possible!

☐ Previously Unable to Code

Select up to 2 Unable to Code Reasons

☐ Awaiting CDM
☐ Blank - Exam
☐ Blank - HPI
☐ Blank - T Sheet
☐ Illegible - Handwriting
☐ Illegible - Scanned Image
☐ Illegible - Signature
☐ Missing - Attending Procedure Note
☐ Missing - Attending Signature
☐ Missing - T Sheet Both Pages
☐ Missing - T Sheet Page 1

☐ Missing - T Sheet Page 2
☐ Potential Critical Care
☐ See Sticky Note

| NoChargeReason | ProfEM | TechCPT1 | ProfDiag | ChiefComplaint | TechDiag1 | TechDiag2 | Status | RenderingProvi... | BillingProvider | POA | Ex |
|---|---|---|---|---|---|---|---|---|---|---|---|
| Triage Only | 99999 | 36686 | 999 | Y | Y | N | Coded | N | N | N | Sar |
| Legal Blood Draw | 99999 | 99281 | 999 | V70.4 | V70.4 | N | Coded | NO CHARGE MD | NO CHARGE MD | N | Sar |
| Triage Only | 99999 | 11135 | 999 | Y | Y | N | Coded | N | N | N | Sor |
| LWBS | 99999 | Y | 999 | Y | Y | N | Coded | N | N | N | Sor |
| Suture Removal | 99999 | 99281 | 999 | Y | V58.32 | N | Coded | N | N | N | Sor |
| Wound Check | 99999 | Y | 999 | Y | Y | N | Coded | N | N | N | Sor |
| PVT MD/Not seen by ED MD | 99999 | Y | 999 | Y | Y | N | Coded | N | N | N | Sor |
| Client Request | 99999 | Y | 999 | Y | Y | N | Coded | Y | Y | Y | Sor |
| Left Before Triage | 99999 | 99999 | 999 | Y | Y | N | No Charge | N | N | Y | Sor |
| Direct Admit | 99999 | Y | 999 | Y | Y | N | Coded | N | N | N | Sor |
| Same Day Visit | 99999 | Y | 999 | Y | Y | N | Coded | N | N | N | Sor |
| LWBS | 99999 | 66000022 | N | Y | Y | V64.3 | Coded | Wolf - 439 | Wolf - 439 | N | St. |
| Suture Removal | 99999 | 99281 | N | Y | Y | N | Coded | N | N | N | St |

# COMPUTER SYSTEM FOR RULE-DRIVEN EMERGENCY DEPARTMENT CODING

BACKGROUND

1. Field of the Invention

The present application relates to, inter alia, systems and methods for Emergency Department coding.

2. Background Discussion

Emergency departments perform numerous medical treatments and procedures. In contrast to other types of medical facilities, emergency departments tend to handle a very wide range of medical issues—i.e., from head colds and viruses, to seeing of patients of other doctors when regular doctor's offices are closed (i.e., thousands of doctors offices even have voicemail messages directing patients to emergency departments after hours when timely treatment is required), to addressing physical injuries related to accidents and/or traumas, etc. As such, emergency departments need to document an extremely wide range of treatments, procedures and diagnoses. In particular, in order to properly a) bill patients and b) have insurance companies reimburse for such billing to patients, it is important that such treatments and diagnoses are properly recorded. However, due to the vast range of treatments, procedures, and diagnoses handled by Emergency Departments, this has proven to be a very difficult task for Emergency Departments.

Moreover, to compound this already vexing problem, Emergency Departments face other difficulties not experienced by most other medical facilities: a) patients frequently arrive without any pre-established appointment scheduled, such that it is frequently more difficult to accommodate fluctuations in workload (including handling of paperwork related to billing) for patients); b) patients often have time-sensitive emergencies requiring immediate treatment and care, such that it is frequently more difficult to process paperwork related to billing, etc., more expeditiously; and c) Emergency Departments often handle much greater volumes of patient visits than other medical facilities.

As a result, Emergency Departments often have difficulty to properly document patient visits and treatment in a manner to ensure that insurance carriers will reimburse the facility for their services and treatment. In situations where services and treatments are not properly documented (i.e., including the incorporation of proper medical "Codes" indefinable by insurance carriers), then the Emergency Department may not be compensated for that expense. As such, Emergency Departments can lose millions of dollars annually due to such difficulties.

Prior to the present invention, Emergency Departments have hired experienced individuals as "Coders" to have such individuals review all documentation prepared by the ED physicians and staff to ensure that the documents can be used to create proper bills for patients, which bills are appropriate in light of various insurance carrier rules and guidelines to ensure as much reimbursement as possible. Coders can, thus, often perform tasks such as review of medical record documentation for proper diagnosis and procedure code selections to provide billing, coding and auditing support to medical facilities for both inpatient and outpatient facility and professional billing functions.

Even though professional Coders are typically employed, there can still be many difficulties in the proper coding and obtaining of reimbursements from, e.g., insurance companies related to such treatments and procedures. Coding in Emergency Departments is rather involved, and individuals that perform such coding often require certification to become coders. In addition, there are even certain companies that have been established to provide coding expertise and assistance to Emergency Departments, such as, e.g., Medical Reimbursement Systems, Inc. (MRSI), the present assignee, which provides emergency physician coding and related billing and follow up for both physicians and facilities. Such coding includes, e.g., both local and national emergency medicine coding and reimbursement issues.

However, prior to the present invention, which greatly facilitates coding capabilities and greatly improves quality and accuracy, coding has been a very complicated function and operation.

SUMMARY

The present invention improves upon the above and/or other background technologies and/or problems related to, e.g., Emergency Department coding through the provision of a Computer System For Rule-Driven Emergency Department Coding.

Among other things, the preferred embodiments provide a computer system whereby Coders can quickly and efficiently review, manage and modify patient record documentation electronically via a graphical user interface (GUI) provided on a computer display or monitor. In this manner, the Coder(s) can create electronic data files and Charge Reports that are used, e.g., by facilities to effect billing to patients and to prepare documentation to seek reimbursement from medical facilities.

In the preferred embodiments, the computer system can automatically populate assorted data into records being created by Coders (e.g., by use of scanning of physical documents and optical character recognition of certain data fields) in conjunction with cross-correlation with other databases, such as, e.g., client accounts, insurance databases, etc.

In addition, in the preferred embodiments, the computer system can automatically provide suggested coding to Coders, can provide coding search tools to Coders to facilitate identification of proper codes, can provide suggestions to Coders (e.g., warning messages, reminders and/or the like) to help guide coders, can create reports and feedback to facilities based on, e.g., compilations of Coder records, etc., and can provide a variety of other functions and advantages over prior methods.

In addition, in the preferred embodiments, the computer system can provide for enhanced review of coder work product, such as, e.g., keeping electronic records of each coders activities and work product, allowing for management review of coders (e.g., the system can have product of junior coders saved and only accepted upon log-in and approval by a supervisor in some embodiments), and can facilitate communication of issues and concerns between coders, management and facilities (e.g., the system can have coders input requests and/or comments to managers and/or to facilities).

According to some embodiments, a computer system for rule-driven emergency department coding, comprising: a) at least one computer configured to present at least one graphical user interface to an Emergency Department Coder via at least one computer display; and b) the at least one graphical user interface including a Coding Template screen having a plurality of user-selectable items in non-code format whereby a Coder can identify appropriate codes upon selection of one or more user-selectable items in non-code format. Preferably, the at least one computer includes a central server and at least one remote computer connected to the central server, the at least one remote computer having an attached display upon which the graphical user interface is displayed to the Coder.

In some examples, the Coding Template is configured to present the plurality of user-selectable items in plain language with regions for a user to click to select one or more of the user-selectable items in plain language. In some examples, the regions for a user to click include electronic check boxes or buttons. In some examples, the system further includes means for transmitting data entered into the Coding Template by the Coder for review by another individual. In some examples, the system is configured to identify codes that are inappropriate and/or invalid to be used together. In some examples, the system is configured to identify improper correlation between procedural codes and diagnosis codes. In some examples, the system is configured to identify codes that are likely to be used together. In some examples, the system is configured to identify possible correlation between procedural codes and diagnosis codes. In some examples, the system further includes a search tool via which a Coder can search for applicable Codes for entry or selection.

According to some embodiments, a method of providing rule-driven emergency department coding is performed that includes: a) providing at least one computer configured to present at least one graphical user interface to an Emergency Department Coder via at least one computer display; b) having the at least one graphical user interface including a Coding Template screen having a plurality of user-selectable items in non-code format whereby a Coder can identify appropriate codes upon selection of one or more user-selectable items in non-code format; and c) having a Coder identify appropriate codes upon selection of one or more user-selectable items in non-code format. In some examples, the method further includes having the Coding Template present the plurality of user-selectable items in plain language with regions for a user to click to select one or more of the user-selectable items in plain language. In some examples, the method further includes transmitting data entered into the Coding Template by the Coder for review by a manager or another individual. In some examples, the method further includes having the system identify improper correlation between procedural codes and diagnosis codes. In some examples, the method further includes having the system identify codes that are likely to be used together. In some examples, the method further includes providing a search tool via which a Coder can search for applicable Codes for entry or selection. In some examples, the method further includes having the method performed by an emergency department facility.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by a way of example, and not limitation, in the accompanying figures, in which:

FIG. 2 is an illustrative coding staff table according to some of the preferred embodiments;

FIG. 3 is an illustrative GUI user interface screen shot that can be presented to, e.g., a coder for, e.g., code entry (such as, e.g., being presented to the coder as a coding template upon the coder's login to the system using the screen shot shown in FIG. 1);

FIG. 4 is another illustrative GUI user interface screen shot that can be presented to, e.g., a coder as a coding template;

FIG. 5 is yet another illustrative GUI user interface screen shot that can be presented to, e.g., a coder as a coding template;

FIG. 8 is an illustrative "Unable to Code Reason" GUI user interface screen shot that can be presented to, e.g., a coder upon clicking "Unable to Code" in the GUI shown in FIG. 7;

FIG. 11 is an illustrative "No Charge Reason" menu that is client specific and includes information listed in a table format according to an illustrative example;

DETAILED DESCRIPTION OF THE PREFERRED EMBODIMENTS

Figure 1:
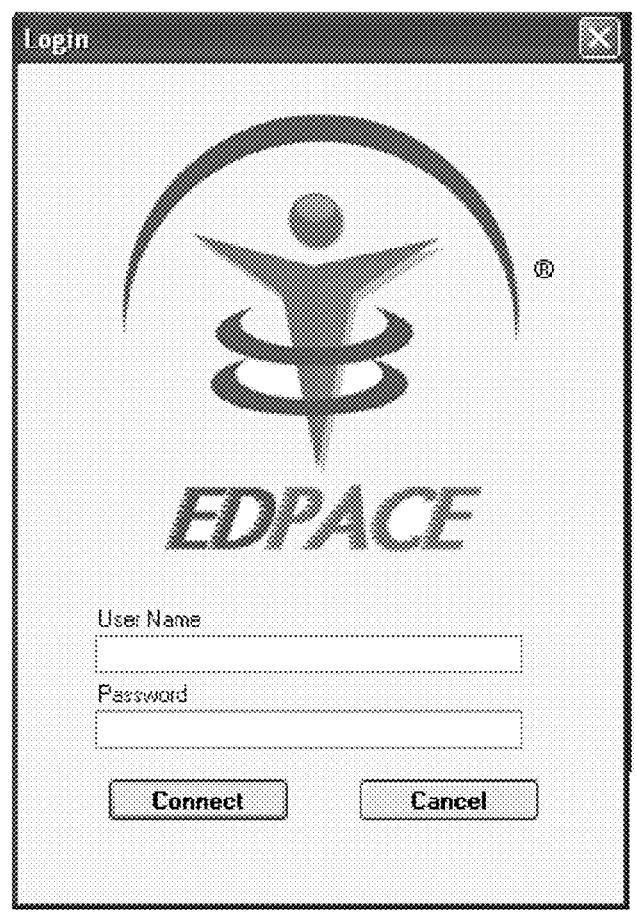
FIG. 1 is an illustrative graphical user interface screen shot that can be presented to, e.g., a coder for login to a computer software system according to some of the preferred embodiments.

While the present invention may be embodied in many different forms, a number of illustrative embodiments are described herein with the understanding that the present disclosure is to be considered as providing examples of the principles of the invention and that such examples are not intended to limit the invention to preferred embodiments described herein and/or illustrated herein.

I. The Preferred Embodiments

In some preferred embodiments, a system is provided that facilitates coding of Emergency Department visit information by coders. In the preferred embodiments, the system is configured such that coders do not need to type in certain information—e.g., upon inputting of certain data, the system preferably automatically populates certain fields.

In preferred embodiments, the system is configured so as to identify and implement different rules based on the particular insurance policy. For example, the system preferably identifies specific "Payer Specific Rules" and/or other rules based on the particular insurance carrier, such as, e.g., MEDICARE or other insurance.

In preferred embodiments, the system is configured such that the coder can simply click on a user friendly graphical user interface (GUI) to identify codes (e.g., 5 digit codes), such as, e.g., by clicking on check boxes and/or other similar GUI functionality.

Preferably, in this manner, a user can readily read and click on appropriate items which are presented in easy to read language (e.g., in plain English), which items relate to the specific codes (e.g., 5 digit codes).

Preferably, the system presents the user a particular screen or pop-up page based on user selection, and once a user clicks on a particular item, the system preferably fills in appropriate information into, e.g., standard form for submission to insurance.

With respect to the standard form, the system preferably identifies the appropriate form based on information provided, such as, e.g., the particular insurance carrier. For example, BLUE CROSS can have a different form from MEDICARE and so on. In some illustrative embodiments, the system creates a CTS 1500 FORM that is a common way to transmit information to insurance carriers.

In some embodiments, a coder's work product can be sent up for review by another individual, such as, e.g., a manager or the like.

In some embodiments, the system is configured to present pop-ups or warning messages based upon user selection.

In some embodiments, the system is configured to provide feedback that can be used by and/or helpful to the Emergency Department. For example, such feedback could provide assistance to the hospital. In some embodiments, the system can be used to create informational charts based on data received.

For example, in some embodiments, the system can identify codes that are inappropriate and/or invalid to be used together. For instance, the system can potentially identify improper correlation between procedural codes such as, e.g., CPT Codes (e.g., 5 digit Current Procedural Terminology Codes) and Diagnosis Codes, such as, e.g., ICD Codes (e.g., International Classification of Disease Codes).

In some embodiments, the system is configured to identify codes that are likely to be used together. For example, the system can be configured to identify possible correlation between procedural codes and diagnosis codes. In this regard, some codes are more likely to occur together. As such, upon the user inputting of a particular code, the software is preferably configured to suggest other likely codes to enter (e.g., CPT Codes and/or ICD codes), such as, e.g., in a convenient pop-up window presented to the coder.

Rather than using a computer system to identify combinations of codes as being invalid or the like for conducting of billing, the present system preferably implements such a functionality in a very unique environment related to coding. Among other things, it is highly advantageous to perform this functionality at the coding stage. In particular, it is noted that billing systems are implemented "after" coding systems. The coding systems generate the information that is presented to the billing system. As a result, the preferred embodiments herein can increase performance at billing. Among other things, the preferred embodiments can help to catch issues earlier, such that data sent to billing is in cleaner or better form.

In preferred embodiments, coding to reduce scrubbing of claims is provided.

In some preferred embodiments, the coder transmits files via the internet or via other means and the Emergency Department handles the billing. In preferred embodiments, the system helps to get data into the system cleanly.

In contrast to other medical fields, Emergency Department coding is particularly vexing. Among other things, ER doctors face a plethora of different patient issues and/or ailments, across the entire medical spectrum. As a result, it is much more difficult for Emergency Departments to know all codes and to perform clean coding to carry out billing.

In the preferred embodiments, the system performs the system functions during the coding process.

In some preferred embodiments, a patient may have a visit at the Emergency Department. Within the next 5 days or so, the coding functions are preferably performed, and then within about 1-2 days later, the billing functions are typically performed. With the present system, coding can be readily carried out within 1-3 days after an ER visit, or even in 1-2 days after such an ER visit. Prior to the present invention, coding often took weeks to carryout, and often months to carry out.

As a result, the present invention can greatly speed up the overall billing cycle for Emergency Departments. In addition, the present system can greatly reduce the amount of paper shipment required and/or delays related to such paper shipping. According to preferred embodiments, the system can create electronic charge reports that can be transmitted electronically, e.g., via the Internet, to, e.g., the hospital.

In addition, in some preferred embodiments, the system also sends other information to assist the hospital, such as, e.g.:

1. Feedback;
2. Identification of items that were not able to be coded; and/or
3. Reports.

In some preferred embodiments, all physical ER documents that are to be processed via the coding system of the present invention are preferably scanned and stored in electronic form. In the preferred embodiments, the system is configured to perform optical character recognition of the electronically stored documents to automatically populate certain information. In some preferred embodiments, the system is adapted to have a pre-established knowledge of a location on the form for certain information, such as, e.g., account number. In some preferred embodiments, upon performing of optical character recognition (OCR) techniques or otherwise identifying the account number and/or other information, the system pulls information from another database to automatically populate information. In some embodiments, the system can verify a record by comparison of an account number with what a patient was seen for at an ER—i.e., comparing to ascertain if there is an actual match.

II. Examples of the Preferred Embodiments

Figure 21:
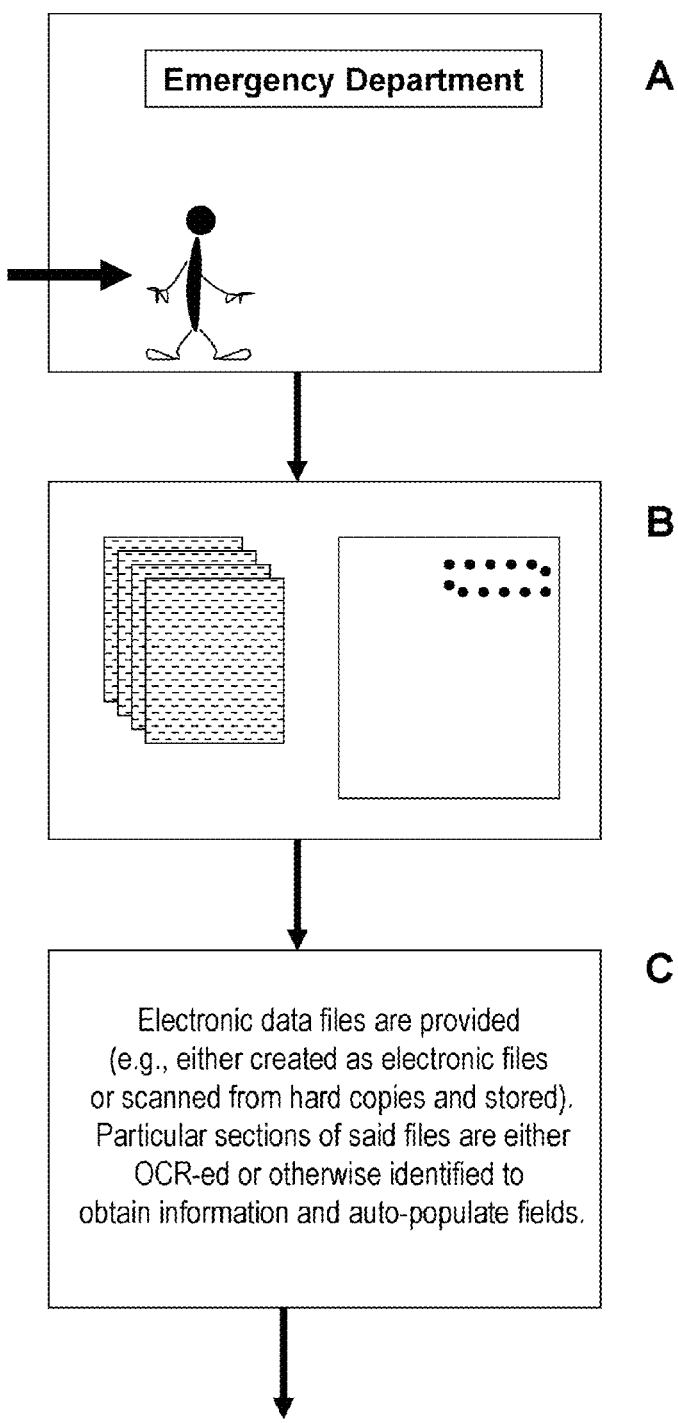
FIGS. 21 and 22 together show a schematic flow diagram to help explain an overall process according to some of the preferred embodiments, with steps A-C shown in FIG. 21 and steps D-F shown in FIG. 22.
Figure 22:
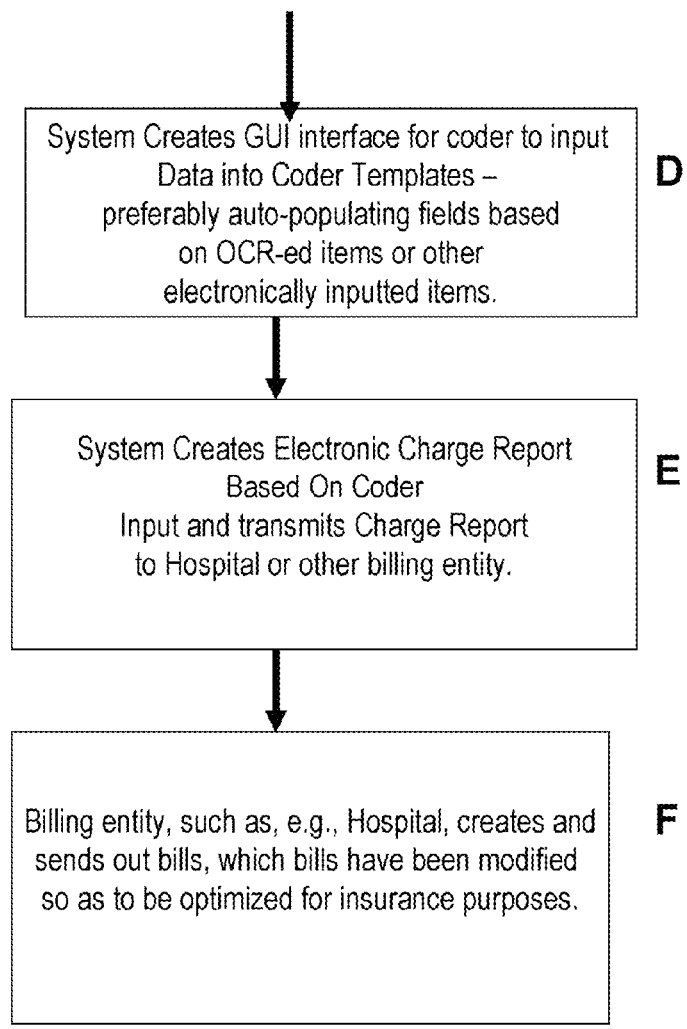

Initially referring to FIGS. 21 to 22, an overall process according to some embodiments of the present invention can include, e.g., the following steps.

A. At an initial step A, a patient enters an emergency department and receives treatment. At this juncture, the emergency department physicians and/or staff enter data and/or information regarding the patient and the treatment of the patient onto either a) physical forms and/or b) electronic data bases.

B. At step B, a plurality (e.g., which can be a very large multitude in many Emergency Departments) of documents are created for the numerous patients that visited the Emergency Department. In some preferred embodiments, these documents involve substantial amounts of physical paper documents that are scanned to create image files thereof. As shown at the right side of the schematic representation of step B, many of these documents are similar in format, and certain sections (such as, e.g., the small top right section shown with dotted lines) can be focused upon to ascertain certain values, such as, e.g., insurance carrier information and/or patient names and/or patient account numbers or the like.

C. At step C, electronic data files are created. By way of example, such data files can be, e.g., part of a server shown in FIG. 19 and/or any other appropriate electronic data base or data storage. As expressed above, the data base(s) can be, e.g., either created as electronic files or scanned from hard copies and stored. As also indicated, particular sections of said files are either OCR-ed or otherwise identified to obtain information and auto-populate fields.

Figure 10:
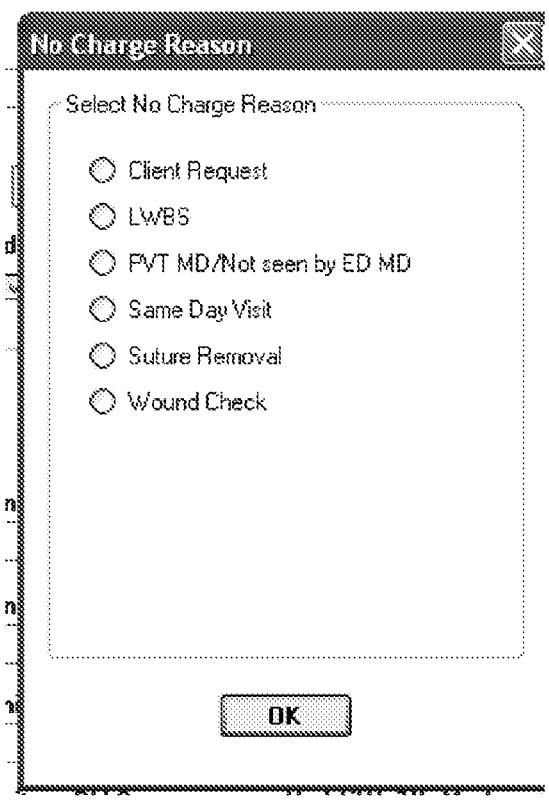
FIG. 10 is an illustrative "No Charge Reason" screen shot that can be presented to, e.g., a coder.

D. At step D, the system preferably creates a GUI interface for coder to input data into Coder Templates (see, e.g., the illustrative Coder Templates shown in FIGS. 3 to 5 which can be, e.g., presented to coders via client devices similar to that shown in FIG. 10. Preferably, the system auto-populates fields based on OCR-ed items or other electronically inputted items as described above. Here, upon, e.g., OCR-ing and identifying some information, such as, e.g., user name or insurance policy or account number, the system can pull other information from other databases, such as, e.g., other patient information and/or other hospital databases in order to auto-populate information for the coder.

E. At step E, after the coder has input all relevant information and data, the system creates electronic Charge Report based on the coder's input. Preferably, the charge report can be electronically transmitted, e.g., via the Internet, to the Hospital or other billing entity for processing.

F. At step F, after receipt of the charge report, the billing entity, such as, e.g., Hospital, creates and sends out bills, which bills have been modified so as to be optimized for insurance purposes based on the information received from said coders in said charge report.

With reference to FIG. 1, the figure shows an illustrative ED PACE Log-In screen. Here, upon entry of an appropriate user name and password, the system will:
 a. determine which clients will be available;
 b. allow specified status options for search criteria; and
 c. auto-populate for productivity tracking and reporting purposes.

With reference to FIG. 2, the system preferably dictates user rights by a "Coding Staff" table:
 a. designates search/view capabilities;
 b. designates status options for completed accounts;
 c. designates log in/access rights.

Figure 3:
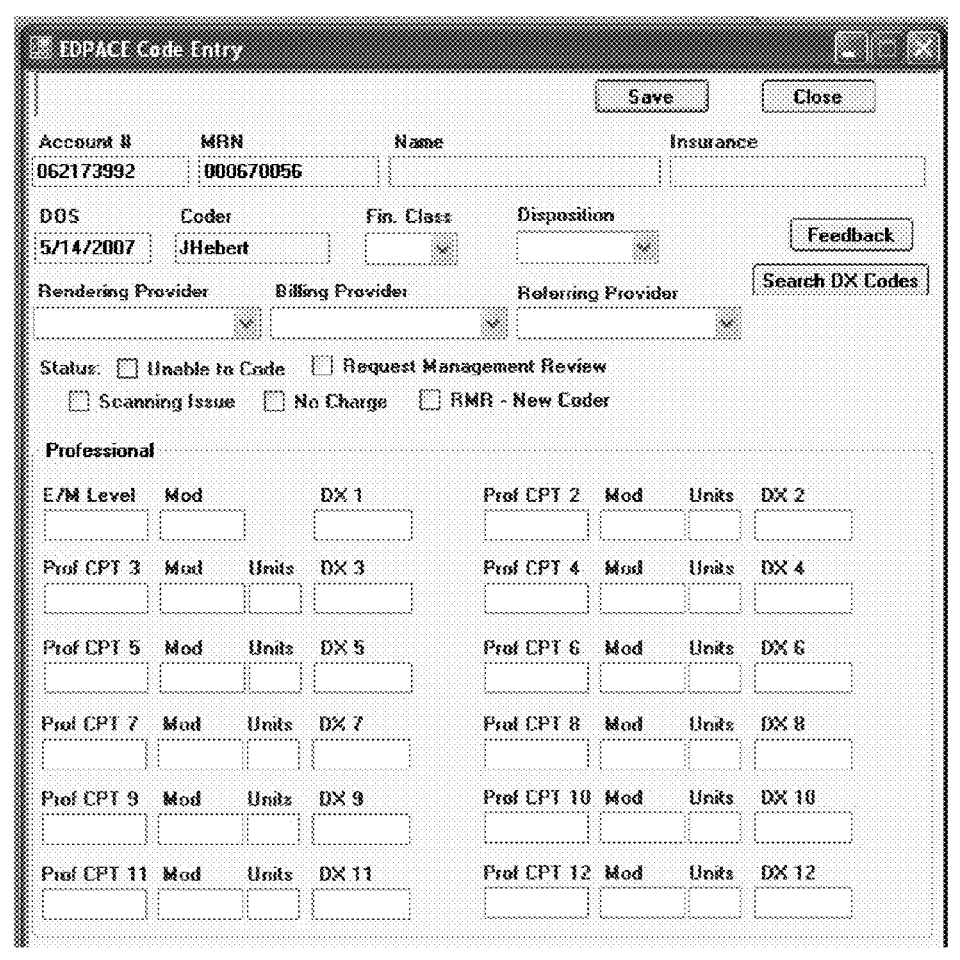

With reference to FIG. 3, the system preferably provides a Professional Coding Template.

Figure 4:
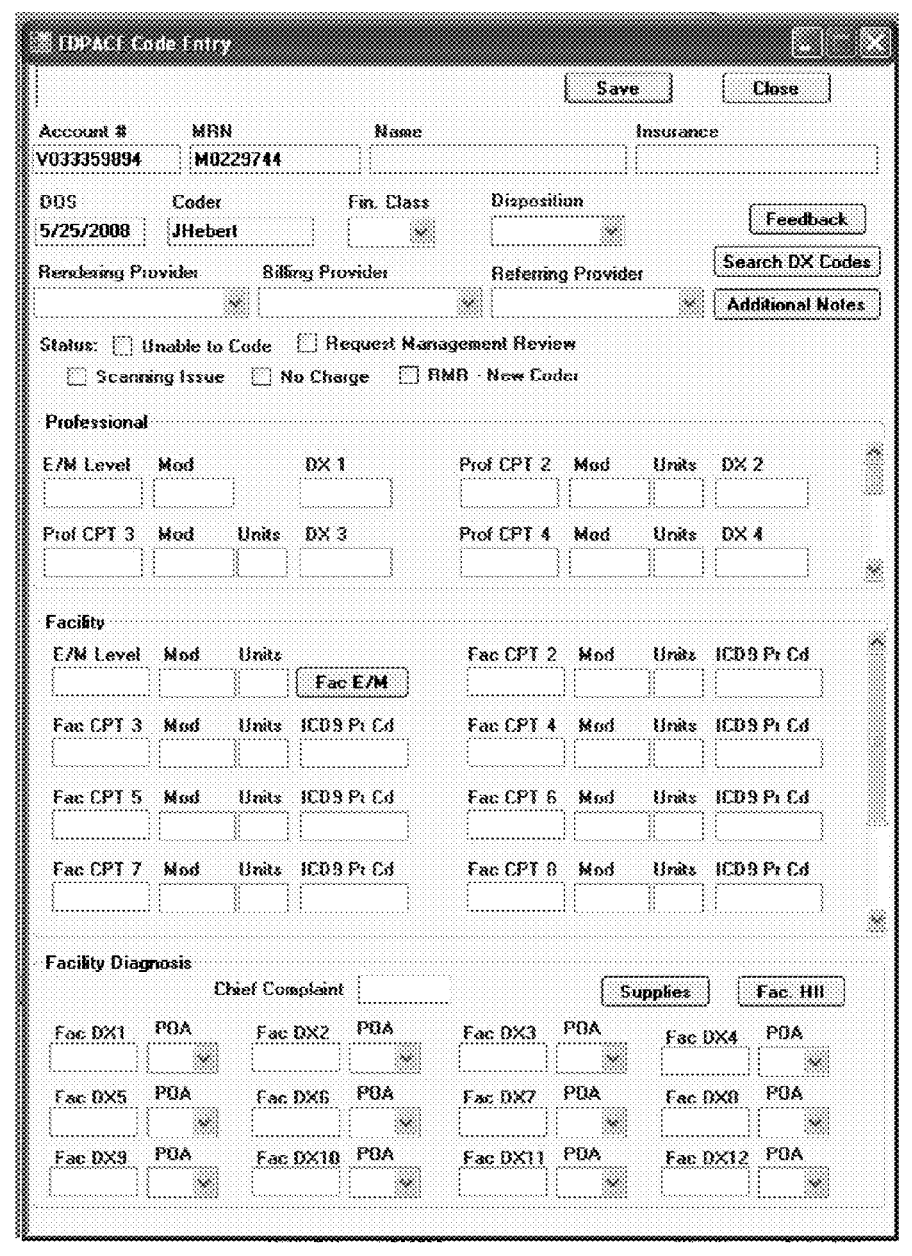

With reference to FIG. 4, the system preferably also provides a Professional and Facility Coding Template.

Figure 5:
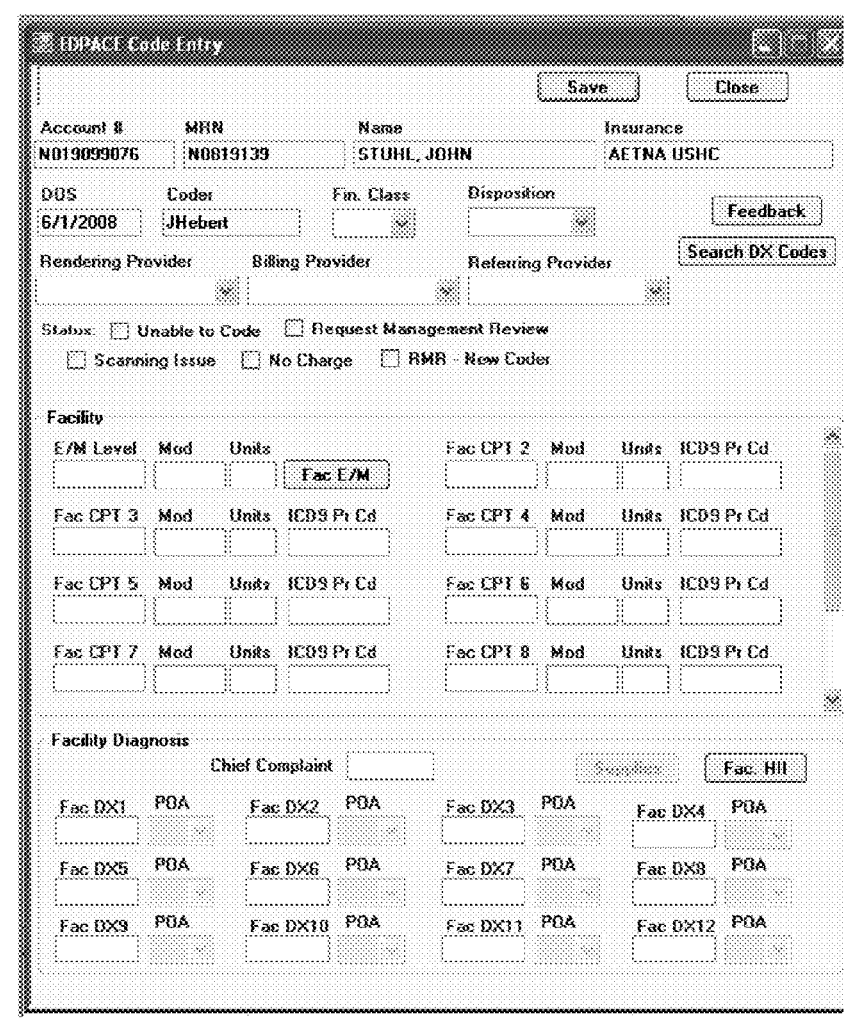

With reference to FIG. 5, the system preferably also provides a Facility Coding Template Patient Information In the preferred embodiments, for all Coding Templates, all Patient Information will be in a "read-only" format, allowing the coder to view the information for reference without editing the information. These fields include Account #, MRN, Name, Insurance and DOS. Additional fields of DOB and Department may also be used per client requirements.

Coder Identification

In the preferred embodiments, each record will have the name of the coder auto-filled as dictated by the log-in information. For specified cases, the coder name will not overwrite any values within that field. For example, in the case of a manager reviewing a record the original coder's name will remain in the "Coder" field.

Data Fields

In the preferred embodiments, the "Financial Class" options can be determined by client requirements. These are most commonly listed as "SP", "WC" and "MVA".

In the preferred embodiments, "Disposition" options are determined by client requirements. These are most commonly listed as "Admitted", "Discharged" and "Transferred". A "Disposition" entry will be required for all "Coded" records.

In the preferred embodiments, all Provider fields will list all active practitioners affiliated with each client, practice or site. These lists may also indicate a provider's credentials, identification number or other information.

Per client and insurance guidelines the Billing and Referring fields may be auto-filled with information driven by the Rendering Provider field value.

Preferably, a "Rendering Provider" and a "Billing Provider" entry will be required for all "Coded" records.

Figures 6, 7:
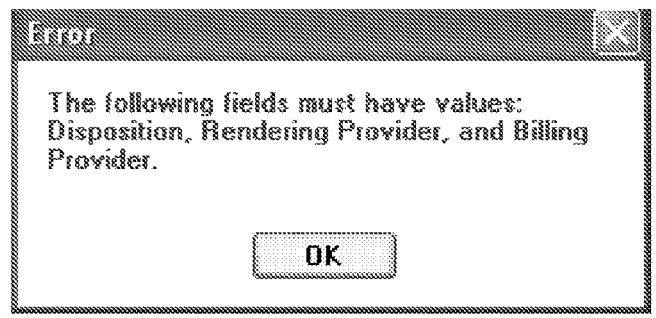
FIG. 6 is an illustrative pop-up screen warning message that can be presented to a coder or the like upon failure to, e.g., complete required fields (e.g., upon saving data input into one of the coding template entry screens of, e.g., FIGS. 3 to 5)
FIG. 7 is an illustrative status option selection screen that can be presented to, e.g., a coder or the like, based on, e.g., the coder's access rights.

In the preferred embodiments, a failure to complete the required fields will result in an educational warning message when the coder chooses the "Save" command—see, e.g., the error message shown in FIG. 6.

Status Options

In the preferred embodiments, there are status options as shown, e.g., in FIG. 7. Preferably, in the All Coding Templates, status options are available as designated by the coder's access rights.

By way of example, an illustrative "Unable to Code" status option can save all data entered in the Coding Template without regard to client specific requirements. A series of "Unable to Code" reasons will be available as specified by each client to reflect missing or incomplete information within the medical record.

For reference, FIG. 8 depicts an illustrative screen in the event that one selects Unable to Code. As illustrated, in such a case, a user can select reasons related to such unable to code as shown.

Figure 9:
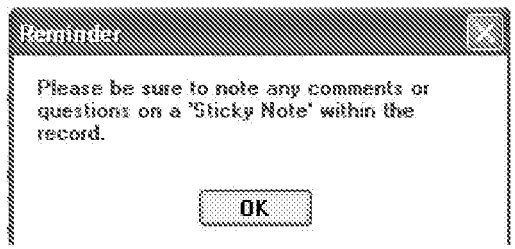
FIG. 9 is an illustrative "Reminder" or "Warning" screen shot that can be displayed to, e.g. a coder to present a reminder or warning in some contexts.

As another example, an illustrative "Request Management Review" status option can save all data entered in the Coding Template without regard to client specific requirements. A notation will preferably be required to allow the coder to further identify any questions or issues encountered while coding the medical record. These notations would be reviewed by a member of management. In some embodiments, a failure to add these additional notations would result in an educational warning message when the coder chooses the "Save" command. By way of example, a reminder or warning can be presented, such as, e.g., similar to that shown in FIG. 9.

As another example, an illustrative "Scanning Issue" status option can save all data entered in the Coding Template without regard to client specific requirements. A notation will preferably be required to allow the coder to further identify any issues with the scanned image of the medical record. These notations would be reviewed by a member of the Scanning Department and corrections made. In some embodiments, a failure to add these additional notations would result in an educational warning message when the coder chooses the "Save" command, such as, e.g., once again, similar to that shown in FIG. 9.

As another example, an illustrative "No Charge" status option can have client specific information auto-filled as indicated by the No Charge reason chosen from the available list. In this regard, an illustrative graphical user interface (GUI) shown in FIG. 10 can be employed to select a no charge reason in preferred embodiments.

Preferably, each No Charge Reason menu will be client specific and all information listed in a table format. By way of example, an illustrative embodiment is shown in FIG. 11.

As another example, an illustrative "Request Management Review (RMR)—New Coder" status option can be used solely for training purposes. This status option will have all client requirements and specified validity checks in place upon choosing the "Save" command. This status option is used only for identifying records coded by trainees. Any assigned reviewer will use this status to capture all records coded by each trainee. In some embodiments, a failure to choose any status option within the Coding Template will result in a status of "Coded" to be automatically assigned. This status option will have all client requirements and specified validity checks in place upon choosing the "Save" command.

Feedback Tool

Figure 12:
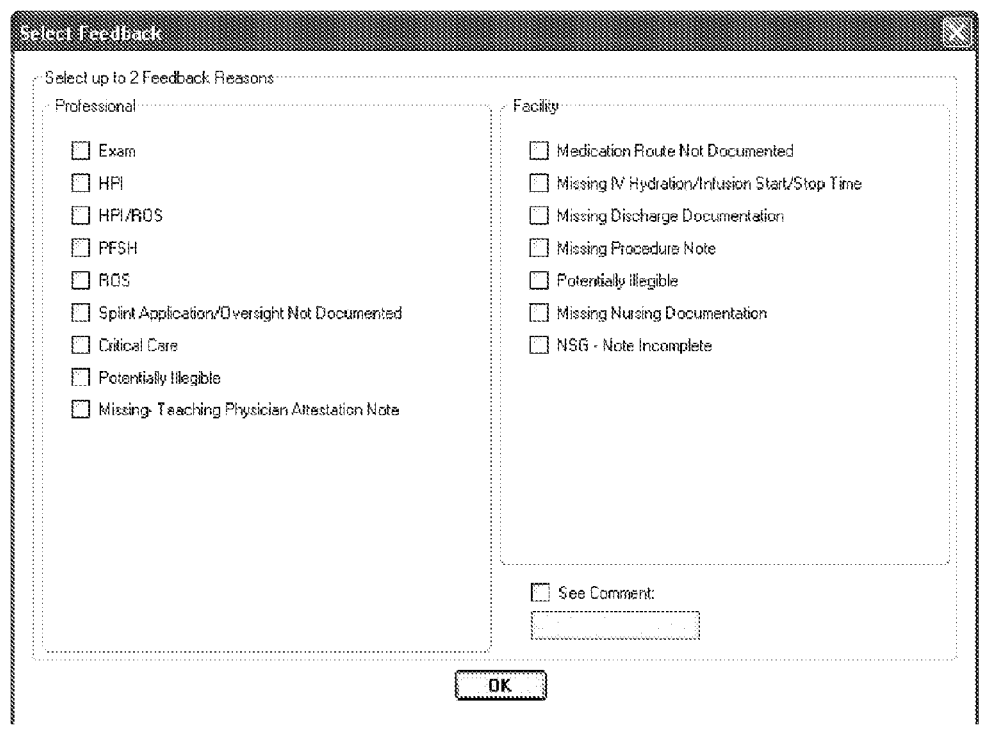
FIG. 12 is an illustrative Feedback form GUI user interface screen shot that can be presented to, e.g., a coder to facilitate selection of feedback reasons.

In preferred embodiments, all Coding Templates will include a "Feedback" tool button listing all client specified Feedback options. By way of example, FIG. 12 shows an exemplary interface to enable users to select feedback reasons. As shown, reasons can be, e.g., in some embodiments classified into professional feedback reasons, facility feedback reasons and/or other categories. In some embodiments, a coder can select to be presented with a GUI similar to that shown in FIG. 12 upon clicking a "Feedback" button similar to that shown at the top right-hand corner of the GUI shown in any of FIGS. 3, 4 and 5.

Search Diagnosis Tool

In some embodiments, all Coding Templates listing a Professional section will include a "Search Diagnosis" tool button to assist the coder in locating diagnosis codes. For example, in some embodiments, a coder can select to be presented with a GUI similar to that shown in FIG. 13 upon clicking a "Search DX Codes" button similar to that shown at the top right-hand corner of the GUI shown in any of FIGS. 3, 4 and 5.

Figure 13:
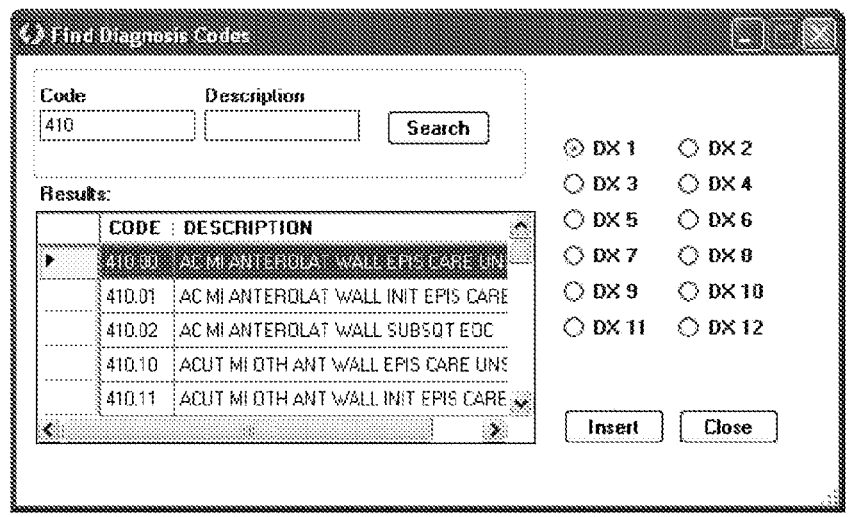
FIG. 13 is an illustrative Search Diagnostics Code GUI user interface screen shot that can be presented to, e.g., a coder to facilitate identification of diagnostic codes.

Preferably, an option to look up diagnosis codes by numeric entries (for partial code, etc.) will be available. For reference, FIG. 13 shows an illustrative interface to enable finding of diagnosis codes. In this illustrative example shown in FIG. 13, a user has typed 410 into the Search field and has been presented with a list of results in the field below.

Figure 14:
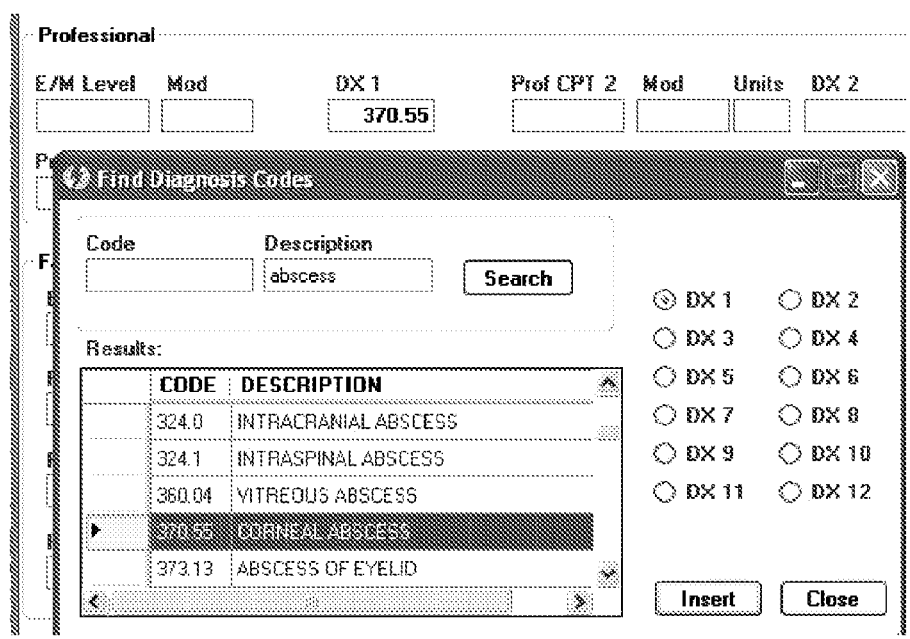
FIG. 14 is an illustrative Find Diagnosis Codes text search GUI user interface screen shot showing an illustrative screen presented to a user upon clicking "search" after entering abscess into a description section of the find diagnosis code screen shown in FIG. 13.

In some preferred embodiments, as shown in FIG. 14, an additional option to look up diagnosis codes by an alpha-character description is preferably available. In this illustrative example shown in FIG. 14, a user has typed abscess into the Search field and has been presented with a list of results in the field below.

Preferably, both Search Diagnosis options will allow the chosen diagnosis codes to auto-fill the specified Professional Diagnosis fields. See, e.g., FIG. 14.

Code Entry Fields (e.g., CPT Fields)

Figures 15, 16, 17, 18:
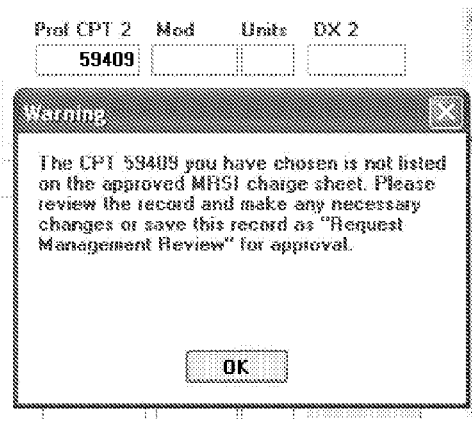
FIG. 15 is an illustrative blown-up portion of a Coding Template screen to facilitate reference of functions that can be employed to guide entry of proper code values—i.e., showing a portion related to Prof (i.e., for professional) CPT 2.
FIG. 16 is another illustrative blown-up portion of a Coding Template screen to facilitate reference of functions that can be employed to guide entry of proper code values—i.e., again showing a portion related to Prof (i.e., for professional) CPT 2.
FIG. 17 is an illustrative pop-up message that can be presented upon an entry of a CPT code value that is identified as improper and/or not approved to help guide coders.
FIG. 18 shows another illustrative pop-up message that can be presented upon an entry of a CPT code value that is identified as improper due to duplicate entry to help guide coders.

In preferred embodiments, all CPT fields for all Coding Templates (e.g., any of the templates shown in FIGS. 3 to 5) will follow a set format—e.g., only allowing valid codes as described by client coding policies. Preferably, an educational warning message will appear when the coder chooses to move away from the CPT field that holds an entry in a format other than described. See, e.g., the illustrative example shown in FIG. 15 with message "Valid entry is 5 characters!" In particular, FIG. 15 shows a portion of the Coding Template screen for reference—i.e., a portion related to Prof (i.e., for professional) CPT 2.

Preferably, an educational warning message will appear when the coder chooses to move away from the CPT field that holds an entry in a five-character format that is not a valid code. See, e.g., the illustrative example shown in FIG. 16 with message "The CPT that was entered is not valid for the corresponding client!" Once again, FIG. 15 shows a portion of the Coding Template screen for reference—i.e., a portion related to Prof (i.e., for professional) CPT 2.

In some preferred embodiments, certain CPT codes that are not usually performed in an Emergency Department setting will prompt an educational warning message requesting that the coder assign a status of "Request Management Review" so that all documentation might be reviewed. See, e.g., FIG. 17 with illustrative message shown. In this regard, FIG. 17 is an illustrative pop-up message that can be presented upon an entry of a CPT code value that is identified as improper and/or not approved to help guide coders;

In some preferred embodiments, entering of duplicate codes in any CPT field will result in an educational warning message. See, e.g., FIG. 18 with illustrative message shown. In this regard, FIG. 18 shows another illustrative pop-up message that can be presented upon an entry of a CPT code value that is identified as improper due to duplicate entry to help guide coders.

III. Illustrative Architecture

In some preferred embodiments, systems of the present invention can include at least one central computer or server that is configured to perform the functions of the present invention, and at least one remote computer(s) or device(s) can be provided for user entry and input, such as, e.g., a personal computer or the like. In some embodiments, the remote computers can communicate with the central computer or server via the Internet or other private or public network. In some embodiments, the users' remote computer(s) or device(s) can be wired or wireless devices. For example, in some embodiments a user device or station has a wireless transceiver and an antenna for communication via, e.g., the Internet or the like.

Figure 19:
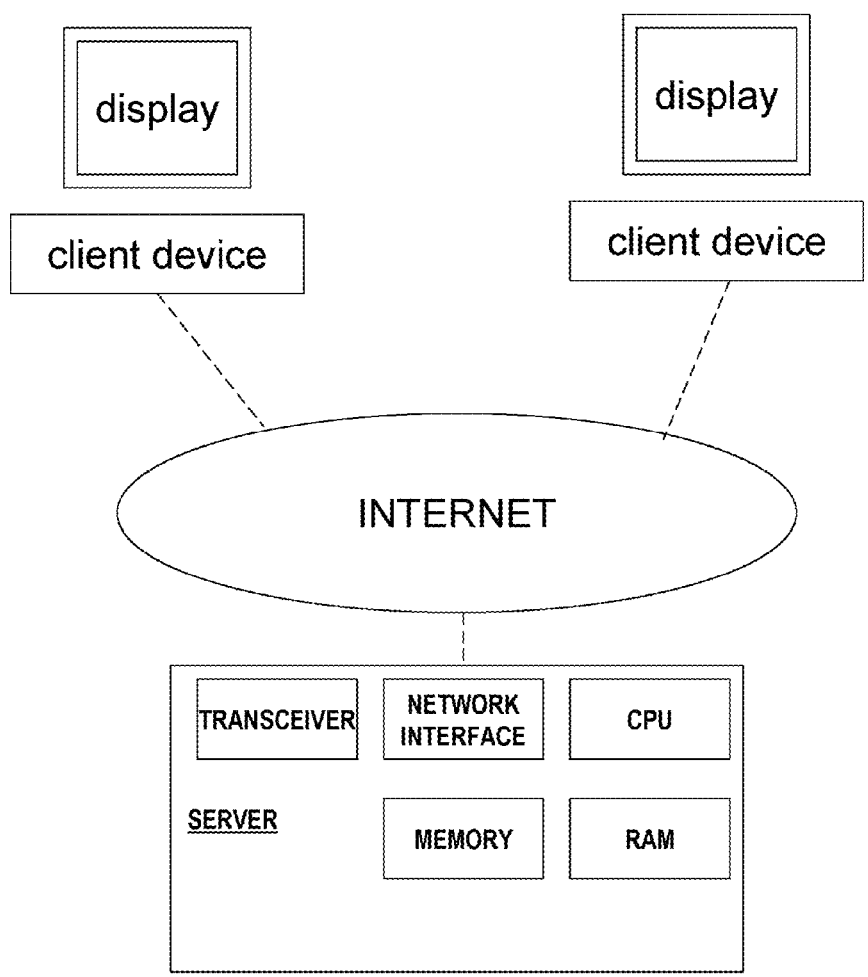
FIG. 19 is an architectural diagram showing system components that be used to implement some embodiments of the invention.

FIG. 19 shows an illustrative system of computers that can be employed to carry out one or more embodiments of the present invention. As shown, in some embodiments, embodiments can be implemented using a client/server functional computer system arrangement. For example, a plurality of client devices (e.g., personal computers, lap top computers, hand-held computers, PDAs and/or the like) can be used to present a graphical user interface (GUI) for a user (e.g., a coder) to input data, to receive data and/or the like. In some preferred embodiments, the client device(s) can communicate with the server via the Internet and/or via another public network, or can connected to the same private network as the server. In some embodiments, the connection is encrypted, password protected and/or otherwise controlled using, e.g., VPN and/or other functionality.

Figure 20:
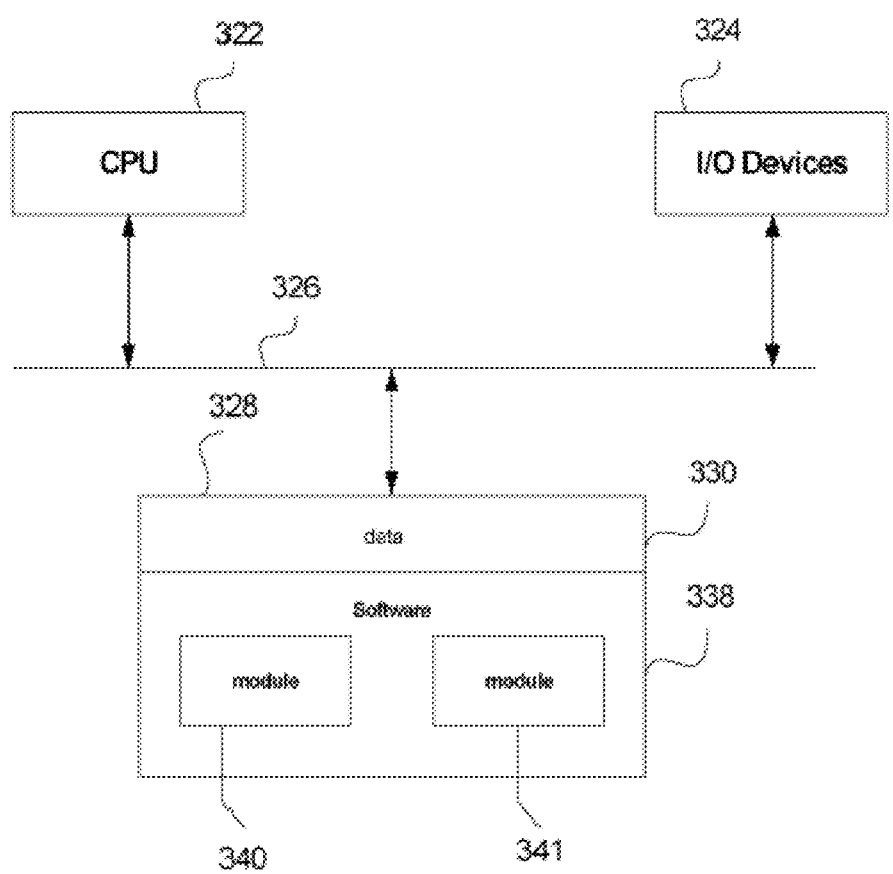
FIG. 20 is a diagram showing illustrative computer components and configurations that can be employed to implement some embodiments of the invention.

In some embodiments, as shown in FIG. 20 the server computer and/or the respective client devices can include, e.g., a central processing unit (CPU) 322, which can communicate with a set of input/output (I/O) device(s) 324 over a bus 326. The I/O devices can include, for example, a keyboard, monitor, and/or other devices. The CPU can communicate with a computer readable medium (e.g., conventional volatile or non-volatile data storage devices) (hereafter "memory") over the bus. The interaction between a CPU, I/O devices, a bus, and a memory 328 can be like that known in the art. Memory can include, e.g., data 330. The memory can also store software 338. The software can include a number of modules (e.g., 340, 341, etc.) for implementing the steps of processes. Conventional programming techniques may be used to implement these modules. Memory can also store the above and/or other data file(s). In some embodiments, the various methods described herein may be implemented via a computer program product for use with a computer system. This implementation may, for example, include a series of computer instructions fixed on a computer readable medium (e.g., a diskette, a CD-ROM, ROM or the like) or transmittable to a computer system via and interface device, such as a modem or the like. A communication medium may be substantially tangible (e.g., communication lines) and/or substantially intangible (e.g., wireless media using microwave, light, infrared, etc.). The computer instructions can be written in various programming languages and/or can be stored in memory device(s), such as semiconductor devices (e.g., chips or circuits), magnetic devices, optical devices and/or other memory devices. In the various embodiments, the transmission may use any appropriate communications technology.

IV. Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A computer system for rule-driven emergency department coding, comprising:
   a) at least one computer configured to present at least one graphical user interface to an Emergency Department Coder via at least one computer display;
   b) said at least one graphical user interface including at least one Coding Template screen having a plurality of user-selectable items in non-code format whereby a Coder can identify appropriate codes upon selection of one or more user-selectable items in non-code format;
   c) at least one database containing image data files of scanned emergency department physical paper forms from emergency department physicians containing scanned medical record information regarding patients and treatment of said patients;
   d) said at least one computer being configured to perform character recognition of said image data files of scanned emergency department forms and to automatically populate and display at least some of said scanned information that is included within said image data files within said at least one Coding Template screen;
   e) said at least one computer being configured to pull other information from said at least one database based on said character recognition of said image data files and to automatically populate and display said other information within said at least one Coding Template screen along with said at least some of said scanned information;
   f) said at least one computer being configured to create an electronic Charge Report based on i) said Coder's identifying of appropriate codes upon selection of said user-selectable items in non-code format, ii) said scanned information, and iii) said other information;
   g) wherein a plurality of said image data files of scanned emergency department physical paper forms have similar document section format and said at least one computer is configured to focus upon particular sub-sections of said image data files of scanned emergency department physical paper forms so as to automatically populate and display certain identified information from within said particular sub-sections;
   h) wherein said at least one computer includes a central server and at least one remote computer connected to said central server, said at least one remote computer having a display upon which said graphical user interface is displayed to said Coder;
   i) wherein said at least one computer is configured to include a search diagnosis tool within said at least one Coding Template screen to assist said Coder in locating diagnosis codes;
   j) wherein said search diagnosis tool is configured to look up diagnosis codes by numeric entries of partial code information by said Coder and/or to look up diagnosis codes by alpha-character description entries by said Coder;

k) wherein said system is configured to enable transmission of data entered into said Coding Template by said Coder for review by another individual; and l) further including said at least one computer causing said at least one Coding Template to include the name of the Coder auto-filled based on log-in information.

2. The computer system of claim 1, wherein said Coding Template is configured to present said plurality of user-selectable items in plain language with regions for a user to click to select one or more of said user-selectable items in plain language.

3. The computer system of claim 2, wherein said regions for a user to click include electronic check boxes or buttons.

4. The computer system according to claim 1, wherein the system is configured to identify codes that are inappropriate and/or invalid to be used together.

5. The computer system according to claim 2, wherein the system is configured to identify improper correlation between procedural codes and diagnosis codes.

6. The computer system according to claim 1, wherein the system is configured to identify codes that are likely to be used together.

7. The computer system according to claim 6, wherein the system is configured to identify possible correlation between procedural codes and diagnosis codes.

8. The computer system according to claim 1, further including a search tool via which a Coder can search for applicable Codes for entry or selection.

9. The computer system according to claim 8, wherein said search tool is configured to list Codes according to similarities to an alphanumeric entry input by the Coder.

10. The computer system according to claim 9, wherein said search tool is configured to list Codes related to certain terminology input by the Coder.

11. A method of providing rule-driven emergency department coding, comprising:

a) at least one computer presenting at least one graphical user interface to an Emergency Department Coder via at least one computer display;

b) said at least one graphical user interface including a Coding Template screen having a plurality of user-selectable items in non-code format whereby a Coder can identify appropriate codes upon selection of one or more user-selectable items in non-code format;

c) said at least one computer receiving inputs from a Coder identifying appropriate codes upon selection of one or more user-selectable items in non-code format;

d) storing in at least one database image data files of scanned emergency department physical paper forms from emergency department physicians containing scanned medical record information regarding patients and treatment of said patients;

e) said at least one computer performing character recognition of said image data files of scanned emergency department forms and automatically populating and displaying at least some of said scanned information that is included within said image data files within said at least one Coding Template screen;

f) said at least one computer pulling other information from said at least one database based on said character recognition of said image data files and automatically populating and displaying said other information within said at least one Coding Template screen along with said at least some of said scanned information;

g) said at least one computer creating an electronic Charge Report based on i) said Coder's identifying of appropriate codes upon selection of said user-selectable items in non-code format, ii) said scanned information, and iii) said other information;

h) wherein a plurality of said image data files of scanned emergency department physical paper forms have similar document section format and said at least one computer focusing upon particular sub-sections of said image data files of scanned emergency department physical paper forms and automatically populating and displaying certain identified information from within said particular sub-sections;

i) further including said at least one computer having a central server and at least one remote computer connected to said central server, said at least one remote computer having a display upon which said graphical user interface is displayed to said Coder;

j) further including said at least one computer including a search diagnosis tool within said at least one Coding Template screen to assist said Coder in locating diagnosis codes;

k) further including said search diagnosis tool looking up diagnosis codes by numeric entries of partial code information by said Coder and/or to looking up diagnosis codes by alpha-character description entries by said Coder;

l) further including transmitting data entered into said Coding Template by said Coder for review by a manager or another individual; and m) further including said at least one computer causing said at least one Coding Template to include the name of the Coder auto-filled based on log-in information.

12. The method of claim 11, further including having the Coding Template present said plurality of user-selectable items in plain language with regions for a user to click to select one or more of said user-selectable items in plain language.

13. The method of claim 11, further including having the system identify improper correlation between procedural codes and diagnosis codes.

14. The method of claim 11, further including having the system identify codes that are likely to be used together.

15. The method of claim 11, further including providing a search tool via which a Coder can search for applicable Codes for entry or selection.

16. The method of claim 11, further including having said method performed by an emergency department facility.

17. The computer system according to claim 1, wherein said at least one computer is configured to enable said Coder to select a scanning issue status option whereby said Coder can identify issues related to scanning of said image data files.

18. The computer system according to claim 1, wherein said at least one computer is configured to enable said Coder to input an unable to code status option whereby said Coder can identify matters that are unable to be coded.

19. The computer system according to claim 1, wherein said at least one computer is configured to electronically transmit said Charge Report to a billing entity for billing purposes.

20. The computer system of according to claim 1, wherein said at least one computer is configured to cause said at least one Coding Template to display patient information in read-only format for the Coder to view without editing, including patient name, patient account number, and patient insurance information.

21. The method according to claim 11, further including said at least one computer causing said at least one Coding Template to include the name of the Coder auto-filled based on log-in information.

22. The method according to claim 11, further including said at least one computer enabling said Coder to a select a scanning issue status option whereby said Coder can identify issues related to scanning of said image data files.

23. The method according to claim 11, further including said at least one computer enabling said Coder to input an unable to code status option whereby said Coder can identify matters that are unable to be coded.

24. The method according to claim 11, further including said at least one computer electronically transmitting said Charge Report to a billing entity for billing purposes.

25. The method according to claim 11, further including said at least one computer causing said at least one Coding Template to display patient information in read-only format for the Coder to view without editing, including patient name, patient account number, and patient insurance information.

* * * * *